United States Patent
Tiwari et al.

(10) Patent No.: US 8,501,444 B2
(45) Date of Patent: Aug. 6, 2013

(54) FERMENTATION PROCESS FOR HIGHER YIELD COEFFICIENT OF LIPASE-INHIBITOR WITH RESPECT TO CONSUMED FATTY ACID

(75) Inventors: Sanjay Tiwari, Bangalore (IN); Chittnalli Ramegowda Naveen Kumar, Bangalore (IN); Deepthy Sathyanathan, Bangalore (IN); Anuj Goel, Bangalore (IN); Harish Iyer, Bangalore (IN)

(73) Assignee: Biocon Limited, Bangalore, Karnataka (IN)

( * ) Notice: Subject to any disclaimer, the term of this patent is extended or adjusted under 35 U.S.C. 154(b) by 273 days.

(21) Appl. No.: 12/934,261

(22) PCT Filed: May 22, 2008

(86) PCT No.: PCT/IN2008/000326
§ 371 (c)(1),
(2), (4) Date: Sep. 23, 2010

(87) PCT Pub. No.: WO2009/118743
PCT Pub. Date: Oct. 1, 2009

(65) Prior Publication Data
US 2011/0014664 A1     Jan. 20, 2011

(30) Foreign Application Priority Data

Mar. 26, 2008 (IN) .............................. 740/CHE/2008

(51) Int. Cl.
*C12P 17/02* (2006.01)
*C07D 305/00* (2006.01)
*C12N 1/20* (2006.01)

(52) U.S. Cl.
USPC ..................... 435/123; 549/328; 435/252.35

(58) Field of Classification Search
USPC ............................... 435/123, 252.35; 549/328
See application file for complete search history.

(56) References Cited

U.S. PATENT DOCUMENTS

| 4,598,089 A | 7/1986 | Hadvary et al. |
| 6,844,174 B2 * | 1/2005 | Erdei et al. ................... 435/125 |

FOREIGN PATENT DOCUMENTS

| EP | 1 860 194 A1 | 11/2007 |
| WO | WO 2004/003212 A1 | 6/2002 |
| WO | WO 2007/078263 A2 | 7/2007 |

OTHER PUBLICATIONS

Bailey's Industrial Oil and Fat Products, 6th Ed., Shahidi, ed., John Wiley & Sons, Inc., Hoboken, 2005, Chap. 13, Soybean Oil, Hammond et al.*
Soybean flour, HoneyBee Australis, 2000, http://web.archive.org/web/20001005012137/http://www.honeybee.com.au/Library/pollen/Soybean.html.*
Eisenreich et al., "Tracer Studies with Crude U-$^{13}$C-Lipid Mixtures," *J. Biol. Chem.* (1997), 272(2):867-874, The American Society of Biochemistry and Molecular Biology, Inc.
Goese et al., "Biosynthesis of Lipstatin. Incorporation of Multiply Deuterium-Labeles (5Z,8Z)-Tetradeca-5,8-dienoic Acid and Octanoic Acid," *J. Org. Chem.* (2001), 66:4673-4678, American Chemical Society.

* cited by examiner

*Primary Examiner* — Rosanne Kosson
(74) *Attorney, Agent, or Firm* — Harness, Dickey & Pierce, PLC

(57) ABSTRACT

The invention provides a process for the production of lipase inhibitors via an improvised fermentation process characterized in that a combinatorial feeding of linoleic acid or its esters or salts thereof and an omega-9 fatty acid, preferably oleic acid and/or its derivatives is employed during said process resulting in an improved yield co-efficient, productivity further providing ease of operation.

21 Claims, No Drawings

FERMENTATION PROCESS FOR HIGHER YIELD COEFFICIENT OF LIPASE-INHIBITOR WITH RESPECT TO CONSUMED FATTY ACID

CROSS REFERENCE TO RELATED APPLICATIONS

This application is a 35 USC §371 National Stage application of International Application No. PCT/IN2008/000326 filed May 22, 2008, now pending; which claims the benefit under 35 USC §119(a) to India Patent Application No. 00740/CHE/2008 filed Mar. 26, 2008. The disclosure of each of the prior applications is considered part of and is incorporated by reference in the disclosure of this application.

FIELD OF THE INVENTION

The invention provides a process for the production of lipase inhibitors via an improvised fermentation process characterized in that a combinatorial feeding of linoleic acid or its esters or salts thereof and an omega-9 fatty acid, preferably oleic acid and/or its derivatives is employed during said process resulting in an improved yield co-efficient, productivity further providing ease of operation.

BACKGROUND OF THE INVENTION

Lipstatin is a potent, irreversible inhibitor of pancreatic lipase, a natural product that was first isolated from *Streptomyces toxyricini*. (Weibel et. al (1987) "Lipstatin, an inhibitor of pancreatic lipase, produced by *Streptomyces toxytricini*. I. Producing Organism, fermentation, isolation and biological activity" J Antibiotic (Tokyo) 40 (8): 1081-5. PMID 3680018. Lipstatin gained considerable importance as a key intermediate for the preparation of tetrahydrolipstatin (Orlistat) which is useful in the prophylaxis and treatment of diseases associated with obesity. E. Hochuli, et al describes the structural chemistry of lipstatin (Journal of Antibiotics Vol XL, No. 8 pp 1081-1085).

The fermentative process for its production, a process for its isolation from microorganisms and a process for its hydrogenation to tetrahydrolipstatin are known and described in U.S. Pat. No. 4,598,089. This invention uses a specific strain *Streptomyces toxytricini* NRRL 15443 and describes preparation of a two step vegetative inoculum.

EP 0803567 describes a fermentation process of lipstatin with the help of precursors such as linoleic acid, caprylic acid and N-formyl-L-leucine or leucine. The production of lipstatin is afforded by a *streptomyces* fermentation, process involving feeding of linoleic acid and leucine. Herein, leucine is incorporated into the final molecule whereas linoleic acid forms the backbone of the final molecule. This process typically gives a yield of lipstatin of about 20% (w/w) over the amount of linoleic acid fed.

WO 03/048335 describes another fermentation medium that uses oil in place of free fatty acid for the production of lipstatin.

Consequently, there remains a need for a low-cost, commercially viable fermentation process which provides sufficient nutrient support to the fermenting microorganism to permit high specific productivity of lipstatin from suitable fatty acid precursors or starting material.

Aside from the discussion above, nothing can be drawn from the literature concerning the use of a combination of linoleic acid with another omega-9 fatty acid to significantly enhance production levels of lipstatin. Unlike the methods suggested in the cited references above, the methods of the present invention provide the triple advantage of: (1) Permitting about 100% improvements in the yield coefficient of lipstatin; (2) Improvising productivity as well as the ease of operation (3) yielding a commercially viable process that is scalable.

Accordingly, an objective of the instant invention is to provide a commercially viable process for the production of lipstatin affording higher yields, an improvement of about 100% in yield coefficient and providing ease of operation as well.

SUMMARY OF THE INVENTION

The present invention provides an improved process for the fermentative production of lipstatin, occurring in the fermentation broth by feeding a combination of linoleic acid and an omega-9 fatty acid, preferably oleic acid further maintaining an appropriate residual concentration of said components which permit increase in the productivity of lipstatin.

According to one aspect of the present invention there is provided a process for producing lipstatin comprising:
  a) Conducting fermentation of a medium comprising a microorganism, a carbon source, a limiting nutrient source and providing conditions sufficient to allow growth and maintenance of said microorganism;
  b) Subsequently feeding a combination of linoleic acid and at least one omega-9 fatty acid at a concentration ratio of 0.01-5 g/L and 0.01-10.0 g/L respectively;
  c) Maintaining said residual concentration of linoleic acid and at least one omega-9 fatty acid throughout the fermentation run; and
  d) Obtaining a yield conversion of greater than 20% w/w.

According to one aspect of the invention, the combinatorial feeding of linoleic acid and oleic acid brings about an improvement of about 100% in yield coefficient of lipstatin produced. The feeding can be either intermittent or concomitant.

DETAILED DESCRIPTION OF THE INVENTION

The present invention is related to a fermentation process for production of lipstatin or its derivatives thereof, characterized in that said process involves a combinatorial feeding of linoleic acid or its esters or salts thereof and at least one omega-9 fatty acid.

In another embodiment of the present invention, yield co-efficient of lipstatin or its derivatives obtained is at least about 20%.

In yet another embodiment of the present invention, the yield co-efficient of lipstatin or its derivatives obtained is at least about 20%-70%.

In still another embodiment of the present invention, the omega-9 fatty acid employed in said process is selected from a group comprising oleic acid, eicosenoic acid, mead acid, erucic acid and nervonic acid.

In still another embodiment of the present invention, the omega-9 fatty acid used is oleic acid.

In still another embodiment of the present invention, combination of linoleic acid and at least one omega-9 fatty acid is fed at a concentration ratio of 0.01-5 g/L and 0.01-10.0 g/L respectively.

In still another embodiment of the present invention, the residual concentration of linoleic acid is maintained in the range of 0.01-5 g/L.

In still another embodiment of the present invention, the residual concentration of linoleic acid is maintained in the range of 0.02-0.1 g/L.

In still another embodiment of the present invention, the residual concentration of linoleic acid is maintained in the range of 0.10-0.30 g/L.

In still another embodiment of the present invention, the residual concentration of omega-9 fatty acid is maintained in the range of 0.1-10.0 g/L.

In still another embodiment of the present invention, the residual concentration of oleic acid is maintained in the range of 0.5-1.0 g/L.

In still another embodiment of the present invention, the residual concentration of oleic acid is maintained in the range of 1.0-2.0 g/L.

The present invention is also related to a fermentation process for producing lipstatin or its derivatives thereof comprising steps of:
a. conducting fermentation of a medium comprising a microorganism, a carbon source, a limiting nutrient source and providing conditions sufficient to allow growth and maintenance of said microorganism;
b. Subsequently feeding a combination of linoleic acid or its esters or salts thereof and at least one omega-9 fatty acid at a concentration ratio of 0.01-5 g/L and 0.01-10.0 g/L respectively; and
c. Maintaining said residual concentration of linoleic acid and at least one omega-9 fatty acid throughout the fermentation run.

In still another embodiment of the present invention, the microorganism belongs to *Streptomyces* sp.

In still another embodiment of the present invention, the microorganism is selected from a group comprising *Streptomyces toxytricini; Streptomyces tuirus; Streptomyces vinaceus; Streptomyces virginiae; Streptomyces lateritus; Streptomyces flavovariabilis; Streptomyces janthinus; Streptomyces purpurascens; Streptomyces roseospinus; Streptomyces roseoviolaceus; Streptomyces violaceus; Streptomyces violaceus* subsp. *confinus; Streptomyces violaceus* subsp. *vicinus; Streptomyces violarus; Streptomyces violatus; Streptomyces yokosukanensis; Streptomyces albosporeus; Streptomyces aurantiacus; Streptomyces aureoverticillatus; Streptomyces aurini; Streptomyces cremeus; Streptomyces daghestanicus; Streptomyces fradiae; Streptomyces fragilis; Streptomyces fumanus; Streptomyces glomeroaurantiacus; Streptomyces griseoviridis; Streptomyces niveoruber, Streptomyces peucetius; Streptomyces phaeoviridis; Streptomyces roseiscieroticus; Streptomyces roseoflavus*

In still another embodiment of the present invention, the microorganism is *Streptomyces toxytricini*.

In still another embodiment of the present invention, the fermentation process is having a seed culture stage and a main fermentation stage, said method comprising
a. cultivating a microorganism biomass in said seed culture stage to produce an inoculum;
b. transferring said inoculum into a fermentation medium at said main fermentation stage; and
c. maintaining steady stage conditions at said main fermentation stage, thereby producing a fermentation broth containing lipstatin.

In still another embodiment of the present invention, the steady state conditions are maintained by feeding of one or more carbon sources, nitrogen sources, pH control, foam control, and control of dissolved oxygen.

In still another embodiment of the present invention, the concentration of dissolved oxygen does not impact the yield coefficient of lipstatin or its derivatives obtained.

In still another embodiment of the present invention, the concentration of dissolved oxygen can vary between 0-100%.

In still another embodiment of the present invention, wherein the fermentation medium employed comprises at least one carbon source, one nitrogen source and process conditions sufficient to allow growth and maintenance of the fermenting microorganism.

In still another embodiment of the present invention, the fermentation medium comprises soya bean flour, glycerol and yeast extract.

In still another embodiment of the present invention, the fermentation medium optionally contains an oil or fat source.

In still another embodiment of the present invention, the fermentation medium is free of oil or fat source.

In still another embodiment of the present invention, characterized in that yield coefficient of lipstatin or its derivatives produced is not affected or altered by the presence or absence of the residual concentration of oil or fat source.

In still another embodiment of the present invention, characterized in that the production of lipstatin or its derivatives is not affected or altered by the stage of fermentation at which leucine is added to the fermentation medium.

In still another embodiment of the present invention, characterized leucine is added initially in the main fermentation stage.

In still another embodiment of the present invention, characterized in that the concentration of leucine added in the fermentation medium is at least 0.1 g/L In still another embodiment of the present invention, characterized in that the production of lipstatin or its derivatives is not affected or altered by the concentration of leucine is added to the fermentation medium.

In still another embodiment of the present invention, characterized in that the addition of linoleic acid and at least one omega-9 fatty acid may be incorporated in either in the seed fermentation medium or the production medium.

In still another embodiment of the present invention, characterized in that intermittent or continuous feeding of soya flour extends the production phase of lipstatin or its derivatives by at least 50%.

In still another embodiment of the present invention, the yield of lipstatin or its derivatives obtained is at least 5.0±1 g/L In still another embodiment of the present invention, the conversion of linoleic acid to lipstatin or its derivatives is at least about 20%.

In still another embodiment of the present invention, the conversion of linoleic acid to lipstatin or its derivatives is at least about 10%.

Other than in the claims and in the operating examples, or where otherwise indicated, all numbers expressing quantities of ingredients or reaction conditions used herein are to be understood as modified in all instances by the term "about".

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Lipase inhibitors, such as lipstatin (LST) and analogues thereof, such as tetrahydrolipstatin (THL) and N-formyl-L-leucine (S)-1-[[(2S,3S)-3-ethyl-4-oxo-2-oxetanyl]methyl] octadecyl ester (LOC), are used within the scope of the invention. As used herein, the term "lipstatin" refers to a precursor of orlistat. E. Hochuli, et al describes the structural chemistry of lipstatin (Journal of Antibiotics Vol XL, No. 8 pp 1081-1085).

The process of the instant invention relates to the production of lipstatin and its derivatives thereof. The process of the instant invention also relates to the production of Olipstatin. Particularly, the present invention relates to process of preparing compounds of Formula I, II and III.

Formula I:

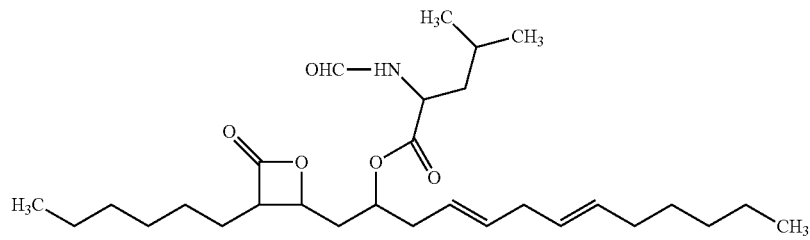

Formula II:

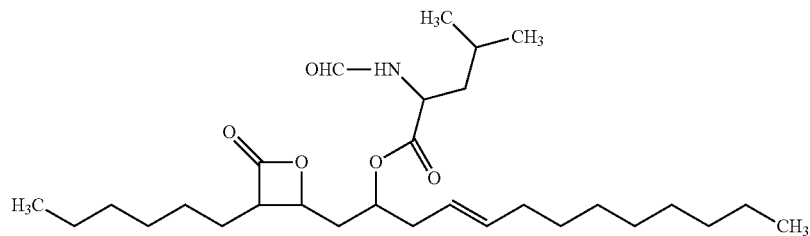

Formula III:

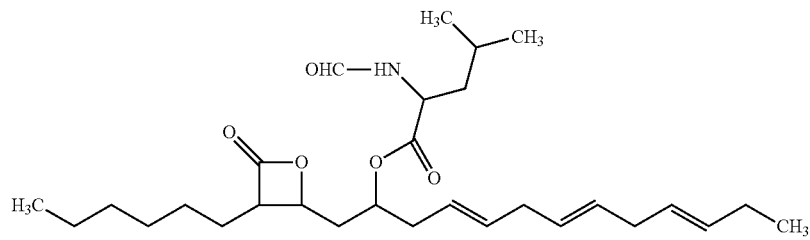

"Omega-9 fatty acids" as used herein are a class of unsaturated fatty acids that have a C=C double bond in the omega-9 position. The present invention encompasses and contemplates the use of omega-9 fatty acids such as Oleic acid 18:1 (n=9) 9-octadecenoic acid, Eicosenoic acid 20:1 (n-9) 11-eicosenoic acid, mead acid 20:3 (n-9) 5,8,11-eicosatrienoic acid, erucic acid 22:1 (n-9), 13-docosenoic acid, nervonic acid 24:1 (n-9), 15-tetracosenoic acid.

"Linoleic acid" as used herein refers to an omega-6 fatty acid. It is polyunsaturated fatty acid with an 18 carbon chain and two cis double bonds, the first double bond is located at the $6^{th}$ carbon from the omega end. The invention contemplates the use of linoleic acid or its esters or derivatives thereof to accomplish the instant objective of increased lipstatin productivity.

As used herein, the term "limiting nutrient source" refers to a source of a nutrient (including the nutrient itself) essential for the growth of a microorganism in that, when the limiting nutrient is depleted from the growth medium, its absence substantially limits the microorganism from growing or replicating further. However, since the other nutrients are still in abundance, the organism can continue to make and accumulate intracellular and/or extracellular products. By choosing a specific limiting nutrient, one can control the type of products that are accumulated. Therefore, providing a limiting nutrient source at a certain rate allows one to control both the rate of growth of the microorganism and the production or accumulation of desired products In yet another aspect of the present invention, microorganisms are selected from the group comprising, fungi (including yeasts), protists, bacteria, or mixtures thereof, wherein the desired fermenting microorganism selected are capable of converting the fermentation substrates under suitable fermentable conditions to produce the desired end product. Most preferred microorganisms include *Streptomyces* sp but not limited to *Streptomyces toxytricini; Streptomyces tuirus; Streptomyces vinaceus; Streptomyces virginiae; Streptomyces lateritus; Streptomyces flavovariabilis; Streptomyces janthinus; Streptomyces purpurascens; Streptomyces roseospinus; Streptomyces roseoviolaceus; Streptomyces violaceus; Streptomyces violaceus* subsp. *confirms; Streptomyces violaceus* subsp. *vicinus; Streptomyces violarus; Streptomyces violatus; Streptomyces yokosukanensis; Streptomyces albosporeus; Streptomyces aurantiacus; Streptomyces aureoverticillatus; Streptomyces aurini; Streptomyces cremeus; Streptomyces daghestanicus; Streptomyces fradiae; Streptomyces fragilis; Streptomyces fumanus; Streptomyces glomeroaurantiacus; Streptomyces griseoviridis; Streptomyces niveoruber, Streptomyces peucetius; Streptomyces phaeoviridis; Streptomyces roseiscieroticus; Streptomyces roseoflavus*. Particularly useful microorganisms of the present invention are microorganisms capable of converting the fermentation substrates provided to lipstatin. The most preferred organism producing lipstatin has been described in U.S. Pat. No. 4,598,089 which is *Streptomyces toxytricini* Preobrazhenskaya & Sveshnikova (see Bergey's Manual of Determinative Bacteriology, 8th edition, page 811).

The present invention provides an improved process for the fermentative production of lipstatin, occurring in the fermentation broth by feeding a combination of linoleic acid and an omega-9 fatty acid, preferably oleic acid further maintaining an appropriate residual concentration of said components which permit increase in the productivity of lipstatin. According to the first step of this process the cells of the lipstatin producing micro-organism are grown in a basal medium/seed medium. In the second step of this process, to this basal medium combination of certain components are added, which either serve directly as biochemical precursors or undergo a biochemical conversion and subsequently serve as precursors of the biosynthetic pathway. Attributed to lesser toxicity imparted by oleic acid relative to linoleic acid, their proper balance of residual concentration ensures that the requirements of energy for growth and maintenance of microorganisms are met. Thereby, the micro-organism is enabled to synthesize the desired end product, lipstatin, in a much higher concentration.

Yield co-efficient of biomass produced over substrate utilized is herein understood to mean the amount of biomass produced in grams dry weight over the amount of substrate utilized in grams. The yield coefficient of fermentation product produced over substrate may be expressed as units or grains of product produced per Kg of substrate used. Particularly, in context of the present invention yield coefficient refers to amount lipstatin produced per amount of linoleic acid consumed.

The basal fermentation medium contains the following necessary components for growth and maintenance of the fermenting microorganism. Suitable sources of metabolizable carbon and energy include but are not limited to glucose, fructose, maltose, glycerol, starch, starch hydrolysates, methanol, short chain alcohols, and mixtures thereof as well as one or more nitrogen sources, such as soybean flour, cotton seed flour, molasses, corn steep powder or corn steep liquor, yeast extract animal by-products and inorganic ammonium salts. Further, macro- and micro-elements may be added to the medium. In one aspect a foam inhibitor is added to the fermentation media in order to prevent the accumulation and build up of foam caused by oxygen sparging of the fermentation broth contained therein.

The carbon source and each of the other essential cell nutrients are added, incrementally or continuously, to the fermentation media, and each required nutrient is maintained at essentially the minimum level needed for efficient assimilation by the growing cells, in accordance with a predetermined cell growth curve based on the metabolic or respiratory function of the cells which convert the carbon source to a biomass. The process constitutes a marked improvement in accelerating and increasing cell production in a given fermentation system.

According to one aspect of the invention culture medium employed herein is substantially free of fats and oils. According another aspect of the invention, the culture medium employed herein comprises oil and an assimilable carbon source as described above, wherein the w/w ratio of oil and an assimilable carbon source is adjusted to regulate lipid biosynthesis by the microorganism. Preferably, the oil is selected from the group comprising natural oil, synthetic oil or a mixture thereof. The natural oil is selected from the group consisting of Sunflower oil, Soya been oil, palm oil, flax oil, rape seed oil, and corn germ oil. The fermentation media of the present invention satisfies the basic nutrient requirements for the growth of the microorganism.

As may be appreciated by one skilled in art, the significant aspects of the invention implemented is not impacted by the residual content of fats in the fermentation medium. The residual content of fats in the fermentation medium can vary from 0-40 g/L.

Various types of auxiliary components may also be employed in the fermentation medium of the present invention in order to further enhance the fermentation process. Examples thereof include, but are not limited to, various types of trace metals, chelating agents, anti-foaming agents, and the like.

In a particular preferred embodiment of the invention, the seed medium contains Soya bean flour—10.0 grams, glycerol—5.0 grams, and yeast extract—5.0 grams in water (1 liter). pH of the medium adjusted to 7.0±0.1.

In a another preferred embodiment of the invention, the production medium contains Soya bean flour—360.0 grams, glycerol—180.0 grams, Anti-foam SAG—6 gram in 6 liters of water, and water (10 liters). pH of the medium adjusted to 7.0±0.1.

In order to obtain a steady state condition during the main fermentation stage, the inventors have found these process parameters, steps and/or variables to include controlling the glucose and/or the total reducing sugar content, maintaining the carbon sources at a suitable minimum level, feeding organic and/or inorganic nitrogen sources, controlling pH, controlling foam level, controlling the mass of the broth by withdrawals and feeding and controlling the dissolved oxygen level by changing the stirring rate and/or aeration rate.

The process may be operated over any pH or temperature range where the fermenting microorganism can grow and catalyze the desired conversion reaction. A preferred and especially advantageous pH range is in the acidic regime, i.e., a pH of about 7 or less and the preferred temperature range is about 27±1° C. The process of this invention may be carried out at a temperature of about 27° C. to about 37° C., preferably about 27° C. Shifts in pH are prevented by addition of bases such as NaOH or acids such as $H_2SO_4$ or HCl. The regulating agent is typically a hydroxide or an organic or inorganic acid. Examples of suitable pH regulating agents are potassium hydroxide, sodium hydroxide and hydrochloric acid. An important aspect of the present invention is the control of a number of process parameters to favor the desired reaction products. Thus, the process or segments of the process can be conducted as continuous operations or various distinct unit operations. The length of time which the fermentation process is allowed to continue depends upon the composition of the fermentation medium, temperature, quantity of inoculum, quantity of product desired, etc. Typically, the fermentation process is conducted for about 8-10 days.

The process of this invention is carried out under sufficiently sterile conditions to ensure cell viability and metabolism.

It is advantageous to maintain a dissolved oxygen level in the production medium of about 20%-80% of air saturation during the major portion of the fermentation. The ability to achieve a suitable dissolved oxygen level may be enhanced by proper adjustment of the aeration and/or agitation rate.

According to one aspect of the present invention there is provided a process for producing lipstatin comprising:
  a) Conducting fermentation of a medium comprising a microorganism, a carbon source, a limiting nutrient source and providing conditions sufficient to allow growth and maintenance of said microorganism.
  b) Subsequently feeding a combination of linoleic acid and at least one omega-9 fatty acid at a concentration ratio of 0.01-5 g/L and 0.1-10.0 g/L respectively.

c) Maintaining said residual concentration of linoleic acid and at least one omega-9 fatty acid throughout the fermentation run.

According to yet another aspect of the invention, the fermentation process is having a seed culture stage and a main fermentation stage, said method comprising a. Cultivating a microorganism biomass in said seed culture stage to produce an inoculum.
b. Transferring said inoculum into a fermentation medium said main fermentation stage.
c. Maintaining steady stage conditions in said main fermentation stage, thereby producing a fermentation broth containing lipstatin.

The crux of the invention resides in the fact that the combinatorial feeding of linoleic acid as well as an omega-9 fatty acid, preferably oleic acid significantly increases lipstatin production.

According to one aspect of the invention, the addition of linoleic acid and oleic acid may be either concomitant or intermittent.

According to one preferred aspect of the invention, preferably the residual concentration of linoleic acid is maintained between 0.10-0.30 g/L, more preferably between 0.01-0.05 g/L and most preferably between 0.02-0.05 g/L. Linoleic acid may be fed in the medium in the range of 0.01-5 g/L.

According to one preferred aspect of the invention, preferably the residual concentration of oleic acid is maintained between 0.25-0.30 g/L, more preferably between 0.50-1.0 g/L, more preferably between 1.0-1.5 g/L, and most preferably between 1.0-2.0 g/L. Oleic acid may be fed in the medium in the range of 0.01-10.0 g/L.

One of objects of the invention is therefore to improve the efficiency of the lipstatin-producing fermentation procedure by forcing the production ability of the microorganism via changing the conditions and the carrying out of the fermentation process. It is another object of the present invention to provide, in either or both the seed and main fermentation stage, the most convenient chemical and physiological conditions for the metabolism by the microorganism. It is a further object of the present invention to provide, in either or both the seed and main fermentation stage, the most convenient chemical and physiological conditions for metabolism by the microorganism by maintaining in a steady state condition, the growth rate and then, for an extended time, a maximal product formation rate.

According to the most significant aspect, the invention provides an improvement of about 100% in the yield co-efficient of lipstatin production. Lipstatin obtainable by the process according to the invention may be in amount of at least 2.0±1 g/L, preferably at least 6.0±1 g/L, more preferably at least 8.0±1 g/L, more preferably at least 13±1 g/L, even more preferably at least 16±1 g/L, most preferably at least 20±1 g/L.

Olipstatin obtainable by the process according to the invention may be in amount of at least 1.0±1 g/L, preferably at least 6.0±1 g/L, more preferably at least 8.0±1 g/L, more preferably at least 13±1 g/L, even more preferably at least 16±1 g/L, most preferably at least 20±1 g/L.

Conversion of oleic acid to lipstatin achieved incorporating aspects of the instant invention yield conversion of at least 10%, at least 20%, preferably at least 25%, preferably at least 30%, preferably at least 35%, more preferably at least 40%, more preferably at least 45%, more preferably at least 50%, more preferably at least 55%, more preferably at least 60%, most preferably at least 65% and most preferably at least 70%. According to yet another aspect of the invention yield conversion obtainable is about 100%.

Conversion of linoleic acid to lipstatin achieved incorporating aspects of the instant invention yield conversion of at least 20%, preferably at least 25%, preferably at least 30%, preferably at least 35%, more preferably at least 40%, more preferably at least 45%, more preferably at least 50%, more preferably at least 55%, more preferably at least 60%, most preferably at least 65% and most preferably at least 70%. According to yet another aspect of the invention yield conversion obtainable is about 100%.

According to one advantage of the instant invention, the stage of fermentation when leucine is added to the fermentation medium and concentration of leucine added does not affect or alter the production levels of desired end product. Thereby, leucine may be added in the initial seed medium itself and not fed during the fed-batch phase or leucine may be added during the fed-batch phase of fermentation as routinely practiced. The concentration of leucine added to the fermentation medium is in the range of 0.1 g/L-40 g/L. According to one aspect of the invention the preferred concentration of leucine added to the fermentation medium is at least 5 g/L, preferably at least 10 g/L, preferably at least 15 g/L, most preferably at least 20 g/L. According to yet another advantageous aspect, the concentration of leucine can be greater than 16 g/L.

According to yet another advantageous aspect of the present invention, linoleic acid, oleic acid and leucine may be incorporated in the seed medium or initial medium itself meant for batch phase of production or may be incorporated during the fed-batch phase of fermentation.

The inventors have discovered that optimal biosynthesis of lipstatin may be performed by adjusting one or more of certain process parameters, steps and/or variables in either or both the seed culture and main fermentation stages of the biosynthesis process.

In a further particularly preferred embodiment of the process of the present invention, intermittent or continuous feeding of concentrated soya flour slurry, extends the productive phase of lipstatin as well as olipstatin by almost 50%. Intermittent or continuous additions of soya flour slurry can extend the batch cycle thereby eliminating the need to add high concentration of soya flour in the initial medium thereby avoiding high oxygen demand in the batch phase of the process.

These and other non-limiting embodiments of the present invention are readily understood by one of ordinary skill in the art upon reading the disclosure and claims provided herein. It is understood that this invention is not limited to the particular methods and processes described, as such desired end products and methods may, of course, vary. It is also to be understood that the terminology used herein is for the purpose of describing particular embodiments only, and is not intended to be limiting.

The invention will be more fully described and understood with reference to the following examples, which are given by way of illustration and are not intended to limit the scope of the invention in any way.

Example 1 a) Preparation of a Seed Culture

A seed medium was prepared containing Soya bean flour 10.0 grams, glycerol 10.0 grams, yeast extract 5.0 grams in water (1 litre). The pH of the seed medium was adjusted to 7.0±0.1 with a NaOH solution. An inoculum medium (500 mL) was filled into a 2000 mL Erlenmeyer flask and closed with a cotton plug and sterilized. Sterilization was performed at 121±2° C., 100±10 kPa for 45 minutes. The sterilized inoculum medium was inoculated with a spore vial suspension of *Streptomyces toxytricini* and incubated at 27±1° C. for 24-36 hours under aerobic conditions.

b) Main Fermentation Process

About 1-2 vol % of the above seed culture was used to inoculate on a laboratory scale. The stirred fermentor with a vessel size of 10 litres contained 6.0 litres of the production medium. The Production medium contained Soya bean flour 360.0 grams, glycerol 180.0 grams, and Antifoam SAG 6.0 gram in 6.0 litre water. The pH of the fermentation medium was adjusted before sterilization to 7.0±0.1 with NaOH. Sterilization was at 121±2° C., 100±10 kPa for 120 minutes. Fermentation was carried out at 27±1° C. for 8-10 days under aerobic conditions. (800 rpm, 1 vvm)

Fermentation was continued for 10 days. Maximum conversion from Linoleic acid to Lipstatin achieved was 19.48%. In another batch (experiment #2) same media composition was used and additionally oleic acid was fed along with linoleic acid and leucine. Fermentation was continued for 10 days. The residual oleic acid was maintained between 0.25-0.30 g/L throughout the batch and the residual linoleic acid levels were maintained between 0.10-0.30 g/L. Maximum conversion achieved was 20.12% and there was no significant difference observed in conversion efficiency. After fermentation for 240 hrs, the concentration of lipstatin was 8.0±1 g/L.

Example 2

In this experiment the seed culture medium and the production medium was same as that used in Example 1. The residual levels of oleic acid were maintained between 0.50-1.0 g/L and the residual linoleic acid levels were maintained between 0.10-0.30 g/L throughout the batch.

The maximum conversion achieved from linoleic acid to lipstatin formation was 39.56%. After fermentation for 240 hrs, the concentration of lipstatin was 8.0±1 g/L.

Example 3

In this experiment the seed culture medium and the production medium was same as that used in Example 1. The residual levels of oleic acid were maintained between 1.0-2.0 g/L and the residual linoleic acid levels were maintained between 0.10-0.30 g/L throughout the batch.

The maximum conversion achieved from linoleic acid to lipstatin formation was 45.46%. After fermentation for 240 hrs, the concentration of lipstatin was 8.0±1 g/L.

Example 4

In this experiment the seed culture medium and the production medium was same as that used in Example 1. The residual levels of oleic acid were maintained between 1.0-2.0 g/L and the residual linoleic acid levels were maintained between 0.02-0.05 g/L throughout the batch.

The conversion of linoleic acid to lipstatin significantly improved to 49.31%. Over and above there was higher production of lipstatin. At the end of fermentation, the titer of olipstatin was 6.05 g/L.

Example 5

In this experiment the seed culture medium was same as that used in Example 1. The Production medium contained Soya bean flour 360.0 grams, glycerol 180.0 grams, L-Leucine 120 grams and Antifoam SAG 6.0 gram in 6.0 litre water. The pH of the fermentation medium was adjusted before sterilization to 7.0±0.1 with NaOH. Sterilization was at 121±2° C., 100±10 kPa for 120 minutes. Fermentation was carried out at 27±1° C. for 8-10 days under aerobic conditions. (800 rpm, 1 vvm)

After the batch phase was completed, linoleic acid was fed throughout the batch. The residual linoleic acid levels were maintained between 0.10-0.30 g/L throughout the batch. At the end of the fermentation (163 hr) the titer of lipstatin was 2.67 g/L.

In another batch (experiment #2) same media composition was used and oleic acid was fed throughout the batch. The residual Oleic acid levels were maintained between 1.0-1.5 g/L throughout the batch. At the end of the fermentation (170 hr) the titer of olipstatin was 1.38 g/L.

Example 6

In this experiment the seed culture medium and the production medium is same as that used in Example 1. Linoleic acid was fed throughout the batch. The residual linoleic acid levels were maintained between 0.10-0.30 g/L throughout the batch. To extend the batch, concentrated slurry (15%) of Soya flour defatted toasted was fed during the fermentation as a supplement of nitrogen. At the end of the fermentation the titer of lipstatin was 13.5 g/L.

In another batch (experiment #2) same media composition is used and only Oleic acid was fed throughout the batch. The residual Oleic acid levels were maintained between 1.0-1.5 g/L throughout the batch. To extend the batch, concentrated slurry (15%) of Soya flour defatted toasted was fed during the fermentation as a supplement of nitrogen. At the end of the fermentation the titer of lipstatin was 5.86 g/L.

It is to be understood that this invention is not limited to the particular methodology, protocols, cell lines, species or genera, and media components described, as such may vary. It is also to be understood that the terminology used herein is for the purpose of describing particular embodiments only, and is not intended to limit the scope of the present invention which will be limited only by the appended claims. The above description is for the purpose of teaching the person of ordinary skill in the art how to practice the present invention, and it is not intended to detail all those obvious modifications and variations of it which will become apparent to the skilled worker upon reading the description.

The instrumentalities reported herein overcome the problems that are outlined above and advance the art by providing a system that suffers less production-related costs and has ease of operation relative to other known methods. This system reduces costs by using described methodologies to achieve a given enhanced conversion efficiency relative to any known process, thus overcoming major disadvantages known in this domain of art.

We claim:

1. A method for making lipstatin or tetrahydrolipstatin (orlistat), comprising the steps of:
   a) conducting fermentation of a medium comprising a lipstatin-producing microorganism and a carbon source to allow growth of the microorganism;
   b) feeding to the microorganism a combination of linoleic acid or esters or salts thereof and at least one omega-9 fatty acid, each at a concentration of 0.01 g/L-10.0 g/L; and
   c) controlling the linoleic acid and the at least one omega-9 fatty acid concentrations throughout the fermentation to obtain a residual linoleic acid concentration of 0.02 g/L-0.3 g/L and a residual omega-9 fatty acid concentration of 0.1 g/L-2.0 g/L in the fermentation process for producing lipstatin or tetrahydrolipstatin;
d) isolating the lipstatin made in at least step (c);
e) optionally converting the lipstatin made in step (d) to tetrahydrolipstatin/orlistat; and optionally
f) determining the yield co-efficient of the produced lipstatin or tetrahydrolipstatin.

2. The method according to claim 1, wherein the yield coefficient of the lipstatin or tetrahydrolipstatin is in the range of 20%-70%.

3. The method according to claim 1, wherein the omega-9 fatty acid is selected from the group consisting of oleic acid, eicosenoic acid, mead acid, erucic acid and nervonic acid.

4. The method according to claim 1, wherein the residual concentration of linoleic acid is maintained in the range of 0.02 g/L-0.30 g/L.

5. The method according to claim 1, wherein the residual concentration of omega-9 fatty acid is maintained in the range of 0.5 g/L-2.0 g/L.

6. The method according to claim 1, wherein the microorganism belongs to a *Streptomyces* species selected from the group consisting of *Streptomyces toxytricini; Streptomyces tuirus; Streptomyces vinaceus; Streptomyces virginiae; Streptomyces lateritus; Streptomyces flavovariabilis; Streptomyces janthinus; Streptomyces purpurascens; Streptomyces roseospinus; Streptomyces roseoviolaceus; Streptomyces violaceus; Streptomyces violaceus* sub-species, *confinus; Streptomyces violaceus* sub-species, *vicinus; Streptomyces violarus; Streptomyces violatus; Streptomyces yokosukanensis; Streptomyces albosporeus; Streptomyces aurantiacus; Streptomyces aureoverticillatus; Streptomyces aurini; Streptomyces cremeus; Streptomyces daghestanicus; Streptomyces fradiae; Streptomyces fragilis; Streptomyces fumanus; Streptomyces glomeroaurantiacus; Streptomyces griseoviridis; Streptomyces niveoruber, Streptomyces peucetius; Streptomyces phaeoviridis; Streptomyces roseiscieroticus* and *Streptomyces roseoflavu.*

7. The method according to claim 1, wherein the method has a seed culture stage and a main fermentation stage, said method comprising:
   a. cultivating a microorganism in said seed culture stage to produce an inoculum;
   b. transferring said inoculum into a fermentation medium at said main fermentation stage; and
   c. maintaining steady state conditions at said main fermentation stage, thereby producing a fermentation broth containing lipstatin.

8. The method according to claim 7, wherein the steady state conditions are maintained by
   a) feeding of one or more carbon sources;
   b) feeding of one or more nitrogen sources;
   c) controlling the pH of the medium;
   d) controlling the foam level; and
   e) controlling the level of dissolved oxygen.

9. The method according to claim 8, wherein the concentration of dissolved oxygen in the fermentation medium is in the range of 20%-80%.

10. The method according to claim 7, wherein the fermentation medium employed comprises at least one carbon source and at least one nitrogen source.

11. The method according to claim 7, wherein the fermentation medium comprises soya bean flour, glycerol and yeast extract, and optionally an oil or fat source.

12. The method according to claim 7, wherein leucine is added to the fermentation medium initially in the main fermentation stage at a concentration of at least 0.1 g/L.

13. The method according to claim 12, wherein the production of lipstatin or tetrahydrolipstatin is not affected or altered by the stage of fermentation at which leucine is added to the fermentation medium.

14. The method according to claim 7, wherein the addition of linoleic acid and at least one omega-9 fatty acid may be incorporated either in the seed culture stage or the main fermentation stage.

15. The method according to claim 1, wherein the yield of lipstatin or derivative thereof obtained is at least 8.0 g/L.

16. The method according to claim 1, wherein the conversion of linoleic acid to lipstatin or tetrahydrolipstatin is in the range of 35%-50%.

17. The method according to claim 4, wherein the residual concentration of linoleic acid is maintained in the range of 0.1 g/L-0.30 g/L.

18. The method according to claim 5, wherein the residual concentration of omega-9 fatty acid is maintained in the range of 1.0 g/L-2.0 g/L.

19. The method according to claim 3, wherein the omega-9 fatty acid is oleic acid.

20. The method according to claim 1, wherein the yield co-efficient of lipstatin or tetrahydrolipstatin is at least 50%.

21. The fermentation process according to claim 7, wherein the fermentation medium is free of a fat source.

* * * * *